United States Patent [19]
Dorfman et al.

[11] Patent Number: 5,718,976
[45] Date of Patent: Feb. 17, 1998

[54] EROSION RESISTANT DIAMOND-LIKE NANOCOMPOSITE COATINGS FOR OPTICAL COMPONENTS

[75] Inventors: Veniamin F. Dorfman, Stony Brook; Arvind Goel, Buffalo; Donald J. Bray, East Amherst, all of N.Y.

[73] Assignee: Advanced Refractory Technologies, Inc., Buffalo, N.Y.

[21] Appl. No.: 476,660

[22] Filed: Jun. 7, 1995

Related U.S. Application Data

[60] Continuation-in-part of Ser. No. 471,401, Jun. 6, 1995, which is a division of Ser. No. 249,167, May 25, 1994, Pat. No. 5,466,431, which is a division of Ser. No. 695,552, May 3, 1991, Pat. No. 5,352,493.

[51] Int. Cl.$^6$ ............................................. B32B 9/00
[52] U.S. Cl. .................... 428/408; 428/426; 428/446; 428/697; 428/696; 428/699
[58] Field of Search ............................ 428/408, 698, 428/688, 697, 699, 426, 446

[56] References Cited

U.S. PATENT DOCUMENTS

| | | |
|---|---|---|
| 4,191,735 | 3/1980 | Nelson et al. . |
| 4,783,368 | 11/1988 | Yamamoto et al. . |
| 4,816,291 | 3/1989 | Desphandey et al. . |
| 4,822,466 | 4/1989 | Rabalais et al. . |
| 4,842,937 | 6/1989 | Meyer et al. . |
| 4,877,677 | 10/1989 | Hirocki et al. . |
| 4,897,829 | 1/1990 | Ikoma et al. . |
| 4,915,977 | 4/1990 | Okamoto et al. . |
| 4,948,388 | 8/1990 | Ringwood . |
| 4,960,643 | 10/1990 | Lemelson . |
| 4,961,958 | 10/1990 | Desphandey et al. . |
| 4,980,021 | 12/1990 | Kitamura et al. . |
| 4,985,051 | 1/1991 | Ringwood . |
| 4,992,298 | 2/1991 | Deutchman et al. . |
| 5,002,899 | 3/1991 | Geis et al. . |
| 5,040,501 | 8/1991 | Lemelson .................... 428/408 |
| 5,055,318 | 10/1991 | Deutchman et al. . |
| 5,064,801 | 11/1991 | Juntgen et al. . |
| 5,068,148 | 11/1991 | Nakahara et al. . |
| 5,077,103 | 12/1991 | Wagner et al. . |
| 5,087,434 | 2/1992 | Frenklach et al. . |
| 5,094,915 | 3/1992 | Subramaniam . |
| 5,100,424 | 3/1992 | Jang et al. . |

(List continued on next page.)

FOREIGN PATENT DOCUMENTS 2 158 086  3/1985  United Kingdom .

OTHER PUBLICATIONS

Dorfman, "Diamond–Like Nanocomposites (DLN)", Thin Solid Films, 267-273:212 (1992).
R. d'Agostino, ed., "Plasma Deposition, Treatment and Etching of Polymers", Academic Press, San Diego, 1990.
Dorfman, V.F., et al., Sov. Phys. Dokl., 28 (1983) 743 (English Abstract).
Dorfman, V., "Synthetics of Solid State Structure", Metallurgia, Moscow (1986).
Dorfman, V., et al. Diamond Films '90, Proc. 1st European Conf. on Diamond and Diamond–Like Carbon Coatings, Crans–Montana (1990).
Weissmantel et al. J. Vac. Sci. Technol. vol. A4, 2892.
Dorfman, et al. J. Tech. Phys. Lett., 14:1033 (1988).
Ageev, "Light Induced Variations of Optical Properties of Diamond–Like Films", Surface and Coating Technologies, 47:269-278 (1991).

*Primary Examiner*—Archene Turner
*Attorney, Agent, or Firm*—Nixon, Hargrave, Devans & Doyle LLP

[57] ABSTRACT

An erosion resistant coating for optically transmissive substrates formed from a diamond-like nanocomposite structure which contains interpenetrating networks of a diamond-like carbon matrix stabilized by hydrogen, a silicone glass-like network stabilized by oxygen, and optionally, at least one network formed from elements and compounds from groups 1–7b and 8 of the periodic table.

9 Claims, 5 Drawing Sheets

U.S. PATENT DOCUMENTS

| | | |
|---|---|---|
| 5,101,288 | 3/1992 | Ohta et al. . |
| 5,110,577 | 5/1992 | Tamor et al. . |
| 5,135,808 | 8/1992 | Kimock et al. . |
| 5,137,784 | 8/1992 | Suzuki et al. . |
| 5,142,390 | 8/1992 | Ohta et al. . |
| 5,158,828 | 10/1992 | Sudani et al. . |
| 5,169,579 | 12/1992 | Marcus et al. . |
| 5,171,732 | 12/1992 | Hed . |
| 5,174,983 | 12/1992 | Snail . |
| 5,177,299 | 1/1993 | Kondo et al. . |
| 5,183,602 | 2/1993 | Raj et al. . |
| 5,190,807 | 3/1993 | Kimock et al. . |
| 5,198,285 | 3/1993 | Arai et al. . |
| 5,202,571 | 4/1993 | Hirabayashi et al. . |
| 5,206,083 | 4/1993 | Raj et al. . |
| 5,210,430 | 5/1993 | Taniguchi et al. . |
| 5,219,769 | 6/1993 | Yonehara et al. . |
| 5,243,199 | 9/1993 | Shiomi et al. . |
| 5,256,483 | 10/1993 | Yamazaki et al. . |
| 5,352,493 | 10/1994 | Dorfman et al. . |
| 5,466,431 | 11/1995 | Dorfman et al. .................... 423/446 |

UNCOATED
ALUMINUM
2000 ml

DLN/Al 2000 ml

Hf-DLN/Al 1000 ml

UNCOATED STEEL
2000 ml

DLN/STEEL
2000 ml

Hf-DLN/STEEL
3000 ml

EROSION RESISTANT DIAMOND-LIKE NANOCOMPOSITE COATINGS FOR OPTICAL COMPONENTS

This application is a continuation-in-part of U.S. patent application Ser. No. 08/471,401, pending, filed Jun. 6, 1995 as a divisional of U.S. patent application Ser. No. 08/249,167, filed May 25, 1994 (now issued as U.S. Pat. No. 5,466,431), which is a divisional of U.S. patent application Ser. No. 07/695,552, filed May 3, 1991 (now issued as U.S. Pat. No. 5,352,493).

BACKGROUND OF THE INVENTION

1. Field of the Invention

The invention relates to the use of diamond-like nanocomposite solid state materials as protective coatings for optical components, especially coatings for optically transmissive parts, such as IR windows.

Various devices use infrared (IR) sensors, or "windows" to receive signals for their control remotely. Such sensors are commonly used in connection with devices which move at high speeds, such as aircraft and guided missiles. These devices and others traveling at high velocities expose the protective IR sensor windows to considerable heat loading and erosion due to the impact of particles. The heat demands coupled with the damage sustained from particle collision with the windows often exceeds the capabilities of the windows. Even the smallest atmospheric dust particles can scratch and otherwise have a considerable erosive effect, over time, on the optical transmissivity of components on objects moving at high speeds.

While various materials could be used to overcome the temperature and erosion/abrasion difficulties already described, the choice of suitable materials which are also optically transmissive is restrictive. The need to have such optically transmissive materials located on-board to receive signals while travelling at high speeds present special problems which have yet to be adequately addressed in the field.

Known materials presently used, for example, to make IR transmissive windows include zinc sulfide (ZnS), zinc selenide (ZnSe), germanium (Ge), silicon (Si), diamond, gallium arsenide (GaAs), gallium phosphide (GaP), fused silica ($SiO_2$), aluminum oxynitride (AlON), sapphire ($Al_2O_3$), magnesium oxide (MgO), spinel ($MgO-Al_2O_3$), cubic zirconia ($ZrO_2$-9.4 tool % $Y_2O_3$), lanthana-doped yttria ($Y_2O_3$-9% $La_2O_3$), yttria ($Y_2O_3$), mixed fluoride glasses, and others. However, such materials useful as IR windows often fail due to the thermal shock caused by atmospheric friction at high velocities. Thermally induced tensile stresses are created in the optically transmissive windows from aerodynamic heating of the external surface and the resulting temperature gradient in the material. For example, air-to-air missiles traveling at speeds exceeding Mach 3 develop stagnation temperatures that can vary from about 350° C. (for Mach 3 at 10 km altitude) to more than about 2000° C. (for Mach 6 at sea level). The higher stated temperature excludes the use of some materials operating in the 8–12 μm wavelength region, including ZnS, ZnSe, GaP, and GaAs because of possible chemical decomposition. Even diamond, with its extraordinary optical, thermal and mechanical properties graphitizes and oxidizes in air at temperatures above 650° C.

Aluminum oxynitride, (AlON), a durable polycrystalline optical material, only exhibits high optical transmissivity up to a wavelength of approximately 4 μm, after which transmission falls off steeply. Also, AlON exhibits some bulk optical scattering and wavefront distortion due to suspected periodic variations in material composition (and therefore index of refraction). Sapphire is an optical material with high strength and low scatter. However, suitable optical transmissivity in sapphire is limited to a wavelength of 4 μm. Sapphire's transmissivity also decreases at high temperatures, and increased emissions lower the signal to noise ratio (this also occurs in AlON and spinel).

Although emission from yttria below 5 μm is negligible, yttria has inferior mechanical and thermochemical properties. Workable optical transmissivity in spinel, cubic zirconia, yttria, magnesium oxide, and lanthana-doped yttria is similarly limited to below 6 microns. Thus oxides can therefore only be used in the wavelength range of about 3–5 microns, and are limited by high temperature properties. Further, the bulk thermal conductivity of most of the materials ranges from 7–50W/m-K.

Although diamond possesses thermal conductivities over an order of magnitude higher than other materials, there are many problems with diamond for use as an IR window material. While ZnS and ZnSe are used most often as IR windows due to good optical transmissivity in the IR regions of interest, these materials are "soft", and therefore especially vulnerable in the severe environments of high temperature and erosion due to particle impact at high velocities.

Protective coatings and films which are applied to protect optically transmissive window materials have been tried in order to increase the overall erosion resistance of window materials. Diamond-like carbon (DLC) films have been tried experimentally as protective coatings for IR windows. See Mirtich, et al., *J. Vac. Sci. & Tech.*, A, 4(6), Nov./Dec. 1986. However, DLC films often require high temperatures and atomic hydrogen for deposition, both of which can degrade the substrate material unless interlayers are used. The layers of material between the substrate and the protective coating (interlayers), improve the adherence of the coating to the substrate. Unfortunately, suitable interlayers which complement the (DLC) materials are often difficult to find. Instead, such interlayers also delaminate at high temperatures, further complicating the process.

In addition, the interlayers, or even the DLC coatings themselves may interfere with the high degree of optical transmissivity often required. To be useful, any protective coating, or interlayer for use with optically transmissive windows, must itself be highly optically transmissive.

Further, DLC films typically possess very high intrinsic stress. The lack of sufficiently high intrinsic stress inhibits the deposition of thick, pore-free films such as are usually required for IR window coatings.

SUMMARY OF THE INVENTION

According to the present invention, a method of inhibiting erosion of an optically transmissive substrate is disclosed comprising applying to said substrate a coating made from a class of diamond-like materials formed from interpenetrating networks comprising a diamond-like carbon network stabilized by hydrogen, a silicon network stabilized by oxygen, and optionally at least one network made from dopant elements or dopant compounds containing elements from groups 1–7b and 8 of the periodic table.

In a further feature, the present invention is directed to an erosion resistant coating made from a class of diamond-like materials formed from interpenetrating networks, said networks comprising a first diamond-like carbon network stabilized by hydrogen, a second silicon network stabilized by oxygen and, optionally, at least one additional network of dopant elements, or compounds containing elements from groups 1–7b and 8 of the periodic table.

In still a further feature of the invention, an erosion resistant material made from an optically transmissive substrate and an erosion resistant coating is disclosed, said coating made from a class of diamond-like materials formed from interpenetrating networks, said networks comprising a first diamond-like carbon network stabilized by hydrogen, a second silicon network stabilized by oxygen and, optionally, at least one additional network of dopant elements, or dopant compounds containing elements from groups 1–7b and 8 of the periodic table.

DETAILED DESCRIPTION OF THE INVENTION

Figure 1A:
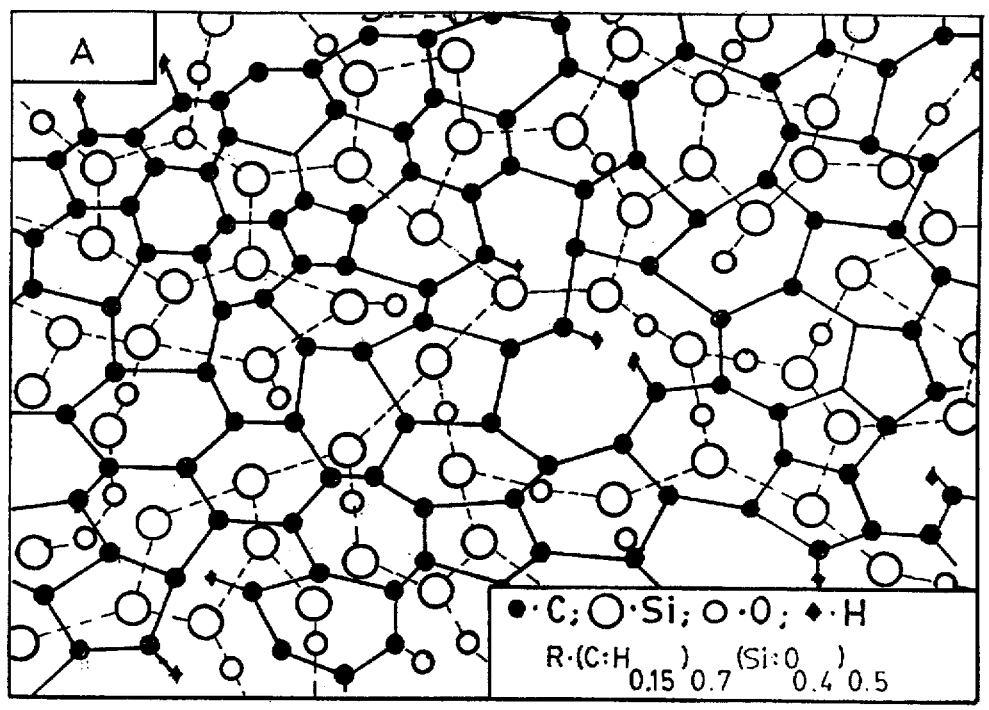
FIGS. 1A–1C are schematic diagrams showing the principle microstructure of two-network (A), intermediate (B), and three-network (C) nanocomposites.

The present invention relates to a method of inhibiting erosion of an optically transmissive substrate comprising applying to said substrate a coating made from a class of diamond-like materials formed from interpenetrating networks comprising a diamond-like carbon network stabilized by hydrogen, a silicon network stabilized by oxygen, and optionally at least one network made from dopant elements or dopant compounds containing elements from groups 1–7b and 8 of the periodic table.

Erosion contemplates the physical damage incurred on a surface due to physical contact with another body. For IR windows, such as on weaponry or other remotely controlled objects which travel at high speeds, mere dust particles at high impact can cause significant, perceptible damage which interferes, over time, with the performance and optical transmissivity of the IR window and its coatings.

Erosion is a destructive force to both metal and non-metal substrates. For example, plastic and ceramic surfaces on both stationary and moving objects must often endure harsh environmental effects, including erosion. Erosion is encountered by substrates which are exposed to particle impact at such velocity that the substrate surface is impacted adversely, such as by physical pitting or chipping. Such erosion may take place on stationary objects exposed to high winds, or objects which themselves travel at high velocities. For example, airplane or missile windows often show the signs of erosion due to impact at very high speeds with, for example, dirt and dust particles.

As well as being erosion-resistant, and highly thermally stable, the erosion-resistant coatings of the present invention are impervious to biological or chemical attack and highly resistant to physical particle bombardment. The resistance of the coatings of the present invention to erosion, reduces the possibility of, for example, physical chipping. This results in the surface of the substrate being less susceptible to exposure from environmental, erosive forces. The coatings have excellent adherence to the substrate and are resistant to thermal shock and elevated temperatures beyond those known to erode known diamond-like coatings.

Optical transmissivity is understood to refer to the ability of desired wavelengths of radiant energy, or light, to pass through. The infrared (IR) transmissive substrates which may be used to make IR transmissive windows, transmit IR energy of wavelengths of from about 0.1μ to about 20μ, preferably 1μ to about 15μ, and most preferably from about 2μ to about 12μ. A window is considered to be IR transmissive if greater than about 75% of IR transmission occurs.

The fundamental structure of the preferred erosion resistant atomic scale diamond-like nanocomposites (DLNs) used to coat the selected substrates is comprised of two or more self-stabilized random networks, each stabilized chemically by additional atomic species, while both networks also structurally stabilize each other. An example of a material with such a structure is the diamond-like nanocomposite (DLN) which is the subject of U.S. Pat. No. 5,352,493 and U.S. Ser. No. 08/249,167 filed May 24, 1994.

In the DLN, a random carbon network, mainly in the form of $sp^3$ "diamond-like" bonds is chemically stabilized by hydrogen atoms, and a glass-like silicon network is chemically stabilized by oxygen atoms, resulting in a purely amorphous structure. "Amorphous" as used herein refers to a random structure or arrangement of atoms in a solid state that results in no long range regular ordering, and lacks crystallinity or granularity. The DLN materials have an amorphous structure and do not contain clusters greater than 10 Angstroms. This absence of clusters at the atomic scale is a key characteristic of the DLN coatings of the present invention. Clusters can destroy the amorphous nature of the structure, can serve as active centers of degradation, and in the case of optical components, can act as light scattering centers.

Therefore, the DLNs contain no clusters or ordering greater than that defined by one-third the radius of the coordination sphere. This structure has been confirmed via electron projection methods, scanning tunneling microscopy, atomic force microscopy, glancing x-ray and electron diffraction techniques and high resolution transmission electron microscopy (TEM). Cluster formation is prevented in the sources, in the primary plasma, in the chamber space, and during film growth.

Figure 1B:
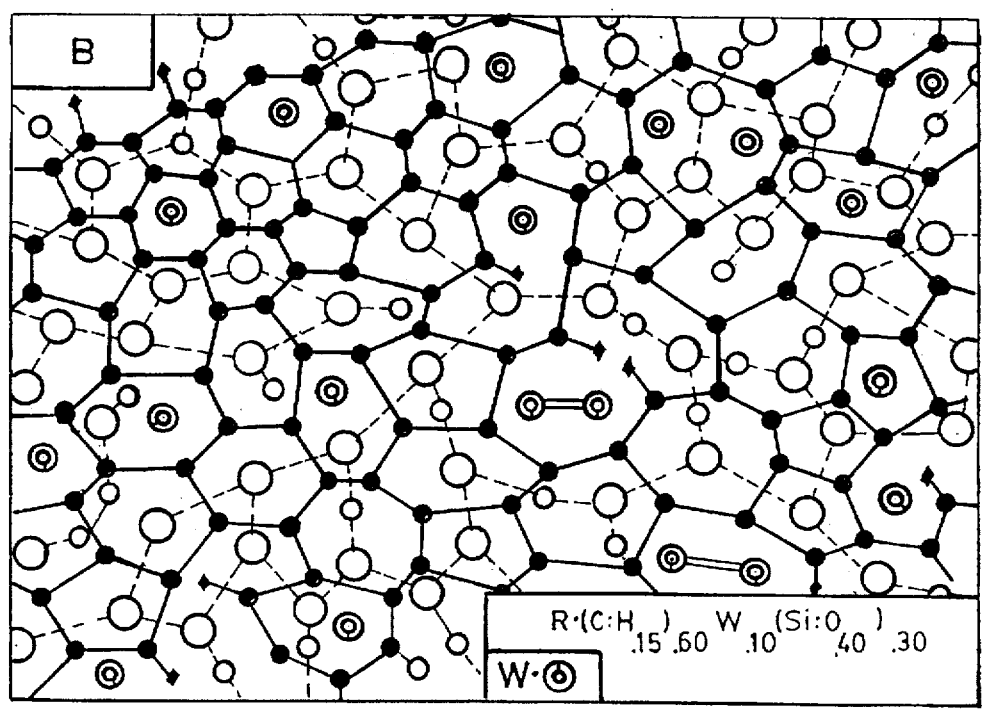
Figure 1C:
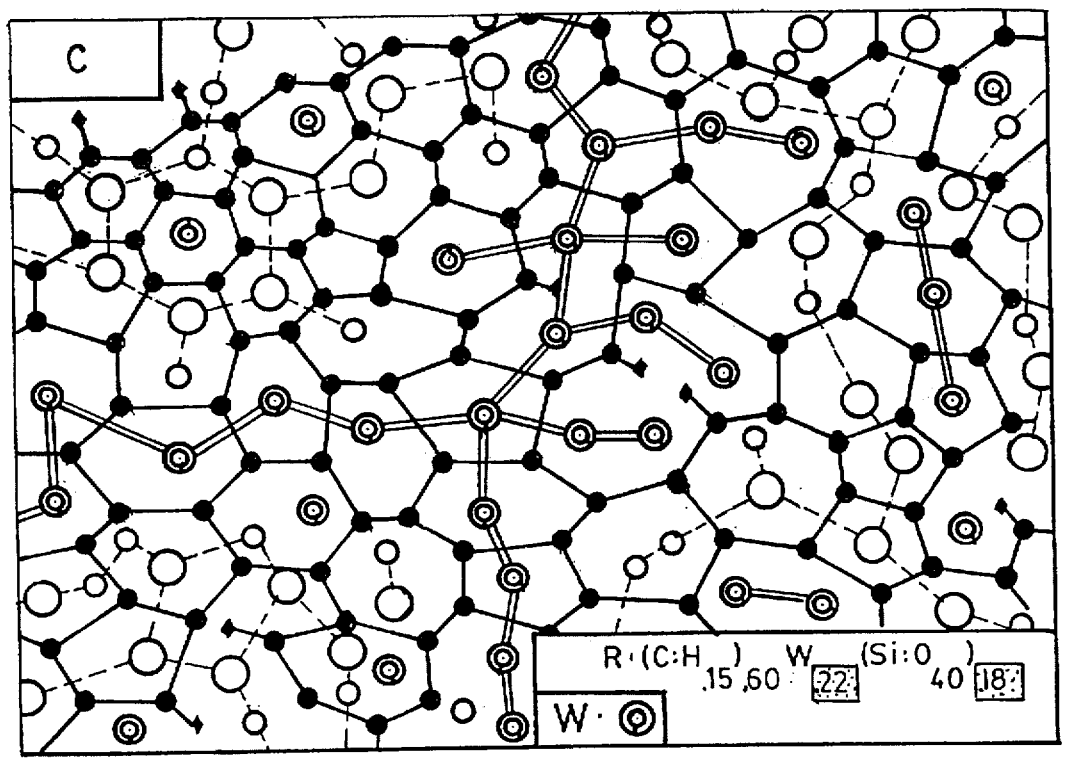

The atomic structure of the class of diamond-like nanocomposite (DLN) solid state materials of the present invention is shown in FIG. 1(A). The materials may have one or more separate disordered networks of dopants, as shown in FIGS. 1(B) and 1(C). The dopants (Me) may be any one or a combination of the metals and non-metals of the groups 1–7b and 8 of the periodic table, and all three types of networks (C-H; Si-O and, if present, the dopant network, Me-Me) are bonded to each other predominantly by weak chemical bonds. The network elements other than the C-H network may be referred to as dopant elements. Silicon and oxygen atoms may also be used in the dopant networks with other elements and compounds. More than one dopant network may be present.

The DLN coatings of the present invention may comprise a two component network: the diamond-like carbon-hydrogen network interpenetrated with the glass-like silicon-oxygen network. A three component network may also be used comprising the Si-O and C-H networks with one or more dopant networks, with the dopants being interspersed with the previously mentioned two interpenetrating networks. In this instance three or more interpenetrating networks will be present in the DLN to form a so-called Me-DLN (metal-diamond-like nanocomposite) network. It is understood that non-metal dopant networks, may be incorporated as the optionally present dopant networks, and will interpenetrate the C-H and Si-O networks.

The three networks (C-H matrix, Si-O matrix and a dopant matrix) are bonded to one another mainly by weak chemical bonds. Carbide formation can be prevented even at metal concentrations as high as 50% (verified using Auger electron spectroscopy, electron spectroscopy for chemical analysis (ESCA), extended x-ray absorption fine structure spectroscopy (EXAFS) and Fourier transform infrared spectroscopy (FTIR)). Again, the properties of these materials can be varied over wide ranges depending on the dopant and the concentration selected, as well as the deposition technique and parameters. As already mentioned, the structure of these composites can be tailored at the atomic level. Therefore, unique electrical, optical, and other desirable solid state properties with desired mechanical strength, hardness and chemical resistance can be imparted on the DLN coatings.

Preferred dopant elements to be used in the Me-DLN network, and which are particularly effective for use as dopants in a corrosion-resistant Me-DLN coating are B, Li, Na, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag and Au; with W, Cr, Zr, Ti and Hf being preferred. Preferred compounds which may be used as dopants include TiN, BN, AlN, ZrN and CrN with TiN, AlN and CrN, being most preferred.

The carbon content in the diamond-like nanocomposite is greater than about 40 atomic % of the DLN. Although the DLN may theoretically be prepared without any hydrogen, the hydrogen content is preferably at least about 1 atomic % and up to about 40 atomic % of the carbon concentration. The sum of the silicon, oxygen and dopant elements and dopant containing compounds is greater than about 2 atomic % of the DLN. In one preferred embodiment, the ratio of carbon to silicon atoms is from about 2:1 to about 8:1, hydrogen to carbon atoms is about 0.01:1 to about 0.4:1, silicon to oxygen atoms is about 0.5:1 to about 3:1, and dopant to carbon atoms is about 0:1 to about 1.5:1. Therefore, in the DLN network, for every 1 part carbon, there is from about 0.01 to about 0.4 parts hydrogen, from about 0.125 to about 0.5 parts silicon, and from about 0.0375 to about 1.0 parts oxygen. In such a scheme, if a third dopant network were present, for every 1 part carbon, there would be from about 0.01 to about 1.5 parts dopants depending upon the desired characteristics to be imparted to the Me-DLN network.

The presence of the glass-like silicon network, stabilized by oxygen, serves to prevent the growth of graphitic carbon at high temperatures, to prevent metal cluster formation in metal-containing three-network nanocomposites, reduce the internal stress in the nanocomposite structure and enhance the adhesion to substrates. This appears to lead to superior adherence of the DLNs of the present invention directly to the substrate material.

As already mentioned, to improve adherence of coatings, DLC coatings often require an intermediate layer between the substrate and the DLC coating. Often, if the DLC coatings are too thick, delamination occurs. Surprisingly, with the DLN coatings of the present invention, adherence is so good that an interlayer is not required. As a result, the DNL coating may be applied directly to the substrate, and more thickly without risking delamination from the substrate. The ability to apply a thicker layer of DLN coating results from the low intrinsic stress due to the Si-O network, and is believed to contribute to the superior erosion resistance of the DLN-coated substrates.

In addition, the elimination of the interlayer increases the flexibility in designing protective coatings which remain optically clear, or for example, optically transmissive to visible light and IR radiation. While many hard DLC-type coatings are known, the DLN coatings of the present invention are themselves IR and visible light transmissive, and therefore do not significantly hinder the original transmissivity of the window substrate material being coated.

The transmissivity of the DLN may be regulated by selection of the precursor used to liberate the constituent C, H, Si and O atoms. Generally, the precursor is selected from the family of polyphenylmethylsiloxanes such that the ratios of elements is best suited for the desired optical transmission in terms of the desired optical wavelength range. For example, for high infrared transmission, especially in the range of from about 8 to about 12μ, the Si-O absorption bands near 10μ must be optimized. Thus a precursor is selected that has a low Si-O to C-H ratio. However, the presence of the Si-O provides low stress and high adhesion, and therefore the Si-O network should not be completely excluded.

If desired, the specific properties of the DLN coatings of the present invention may be tailored or "tuned" by closely monitoring the amount of metal incorporated as the third network during layer deposition to be useful to minimize signature; e.g., minimizing risk of detection by sensing devices. The DLNs of the present invention can be deposited in multilayer and functionally graded modes, with optical and electrical properties tuned in order to obtain certain performance criteria as may be required. Such "tuning" is accomplished by incrementally altering the particular dopant, the dopant concentration, and/or the deposition conditions, such as substrate bias voltage. The DLNs may also have their properties altered or "tuned" when no dopants are included. Such changes in properties in the two-network system can be achieved by altering the deposition conditions such as substrate bias voltage.

The DLNs of the present invention have temperature stability far exceeding that of traditional diamond-like (DLC) materials. For example, crystalline diamond is stable to approximately 1100° C., upon which graphitization occurs. Quartz has long term thermal stability to 1470° C., and short term thermal stability up to 1700° C. Traditional, non-alloyed diamond-like (DLC) films are stable only to about 600° C. before graphitization occurs. By contrast, the DLN materials used to provide the erosion resistant coatings of the present invention have long term stability to 1250° C. and short term stability to 2000° C. Therefore the thermal stability of the DLNs exceeds that of DLCs while preserving the amorphous, diamond-like and optically transmissive state.

Further, in the range of from about 600° C. to about 1000° C., the chemical bonds of the carbon matrix of DLN materials partly change from $sp^3$ to $sp^2$. However, the general structure of the nanocomposite and their "diamond-like" properties are preserved. By contrast, under similar conditions, the usual "diamond-like" carbon (DLC) is graphitized and loses its diamond-like properties. For DLNs exposed to temperatures in the range of from about 400° C. to about 500° C. (preferably 430° C.), a reverse transition is observed, whereby the ratio of $sp^3$ to $sp^2$ is increased.

The density of the C-H and Si-O two network DLN varies from about 1.8 to about 2.1 g/cm$^3$. The rest of the space is taken up by a random network of nanopores with diameters varying from about 0.28 to about 0.35 nm. The nanopore network does not form clusters or micropores. As already mentioned, the properties of the two network DLN may then be tailored by adding dopant. The dopants fill the nanopore network in a random fashion, eventually resulting, at a certain dopant concentration, in an additional network without clusters or microcrystalline grains, even at concentrations as high as 50 atomic %. At concentrations below about 10 atomic %, the dopants are distributed as separate atoms in the nanopores of the diamond-like matrix. The average distance between dopant atoms in this quasi-random structure can be controlled by the concentration of the dopant. When the relative concentration of the dopant element or compound reaches about 20–25 atomic %, the dopants form the third (Me-Me) network in the DLN structure as shown in FIG. 1(C), resulting in a material with diamond-like mechanical and chemical properties.

In the intermediate concentration range, where the dopant concentration is from about 10 to about 20 atomic %, the dopants form a fragmented, random network, without true network-like connectivity. The electronic properties of the fragmented dopant "network" depend strongly on external mechanical loading, pressure and electromagnetic fields. The Me-DLNs with dopant concentrations in the range of from about 1 to about 20 atomic % may be ideal for use as smart materials and sensors. "Smart" materials are understood to be materials that not only sense an external stimulus, but also can react and make appropriate adjustments in response.

The electrical properties of the DLN structures of the present invention can be varied over a wide magnitude (at least 18 orders) from a purely dielectric material to a metallic state while preserving and improving the properties of the DLC state. A transition to a superconducting state, with the absence of electrical resistivity, is observed at low temperatures for certain three-network nanocomposite networks.

Another advantage of the DLNs of the present invention is their relative hardness and durability. The DLNs, especially the metal doped DLNs combine high microhardness with high elasticity. The microhardness values of the DLNs of the present invention range from about 6 to about 30 GPa.

The DLNs may be synthesized via co-deposition by clusterless beams of ions, atoms or radicals of the relevant elements, where the mean free path of each particle species exceeds the distance between its source and the growing particle film surface, and each beam contains particles of well-defined energy. Carbon-containing particle beams can be produced by plasma discharge in a plasmatron and extracted as charged particles by a high-voltage field in a vacuum chamber and directed onto the substrate. At least 50% of the carbon-containing particles have kinetic energy above about 100 eV. The temperature of the substrate during growth should not exceed 500° C.

Figure 4:
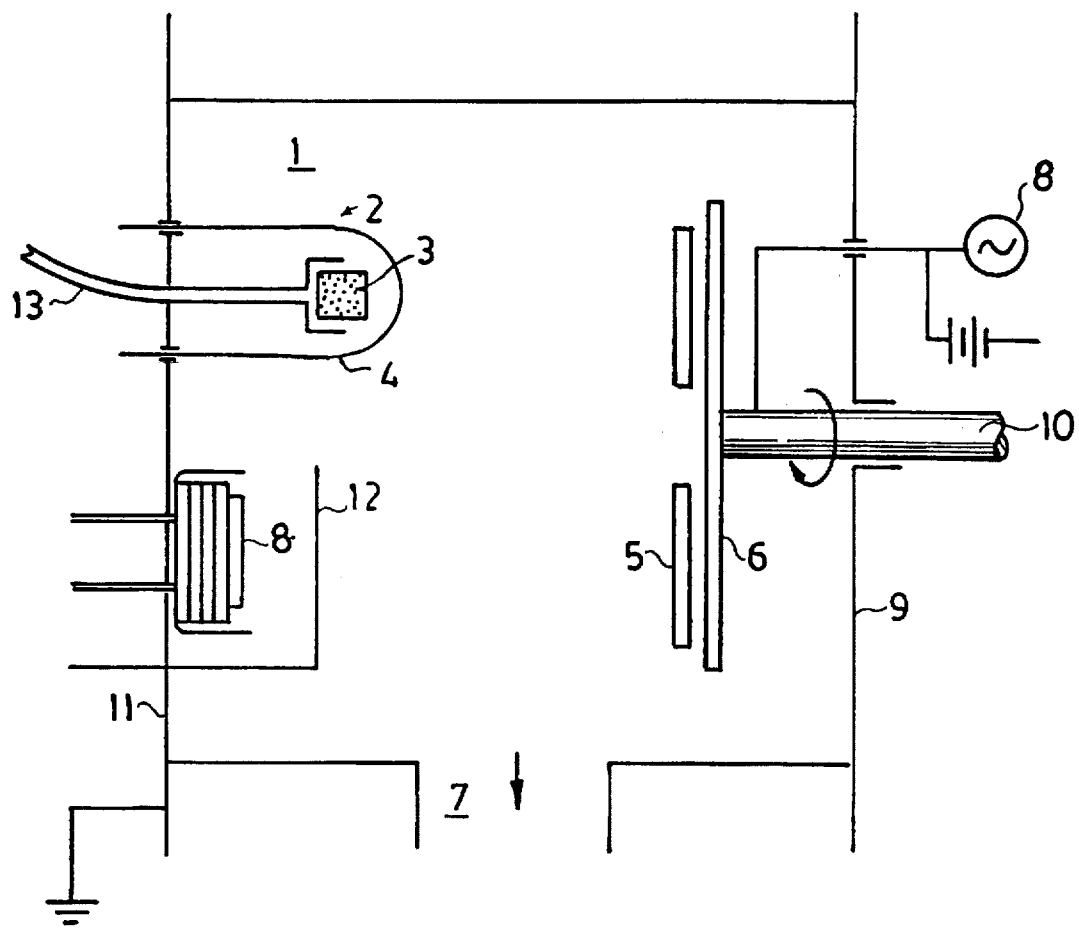
FIG. 4 is a further schematic diagram detailing the method of depositing DLN coatings.

FIG. 4 shows one preferred embodiment of the coating chamber used for the DLN coating deposition process. A vacuum deposition chamber 1 is provided to coat a substrate sample. A precursor inlet system 13, comprises a metal tube and a porous ceramic material 3 through which a liquid precursor, preferably a polysiloxane, is injected. The precursor inlet system 13 is shown incorporated into the chamber through the chamber base plate 11. The thermocathode 2 comprises a resistively heated thoriated tungsten filament 4. Substrates 5 to be coated with DLN film are attached to the substrate holder 6. The power supply 8 is used for biasing the substrates (DC or RF). In practice the system is "pumped down" using normal vacuum pump down procedures. A gate valve (not shown) located on port 7 is closed and the system is backfilled with dry air, nitrogen or argon until the chamber reaches atmospheric pressure. The door of the chamber, 9, is then opened and substrate to be coated 5 are attached to the substrate holder 6 using any of many possible methods (spring clip, screw, clamp, etc.). Special fixtures may be required for substrates of special shapes. The substrate holder is designed in a way that it will also hold a cylinder sample (not shown), which, in operation, rotates both about the axis of the central drive shaft 10, and its own axis which is perpendicular to 10. In this way, the axis of the cylinder would be perpendicular to the axis of 10.

When the substrates are loaded, the door of the chamber is closed. The chamber is then evacuated and the gate valve opened to bring system pressure down to at least $10^{-5}$ to $10^{-6}$ Torr, which is the desired range of system base pressure. When the above base pressure is achieved, argon gas is introduced into the chamber via a needle valve or mass flow controller, until the chamber pressure reaches approximately $5 \times 10^{-5}$ to $1 \times 10^{-3}$ Torr, preferably about $1-3 \times 10^{-4}$ Torr. At this point the filament current, the filament bias and the electromagnet power supply are switched on. The filament current is the current that passes through the thermocathode (also called the filament or the cathode). The filament bias is the constant floating voltage applied to the filament (approximately $-150V$ in relation to ground). Plasma current is measured as the current between the filament and the base plate or ground. This voltage provides the field that moves electrons emitted by the filament to the base plate 11. The electromagnet power supply provides current to the electromagnet, which creates a magnetic field that results in the electron path becoming a spiral, increasing the electron path length and improving the probability of collisions between the electrons and the vapor molecules created due to precursor evaporation. At the same time the substrate bias power supply is switched on.

Switching on these power supplies results in creation of an argon plasma, which is used to clean the substrates prior to deposition. After the required duration of cleaning, the precursor supply is opened. Precursor flow is controlled via a needle valve and occurs due to the difference in pressure between the chamber and the outside atmosphere. Alternative means of precursor delivery, such as a mechanical pump, are also contemplated.

When precursor flow and vaporization in the chamber has stabilized, the argon gas flow is turned off. The ionized precursor vapors form a stable plasma, ions from which are accelerated towards the substrate holder due to the substrate bias. Thus, deposition of DLN film occurs.

Co-deposition of a dopant material is carried out as follows. Argon flow to the magnetron is commenced and power to the magnetron 8 is switched on after the base pressure has been reached. A shutter 12 is used to prevent deposition while the substrate is cleaned via sputtering. When cleaning has been accomplished, the shutter is opened and sputtering is carried out at the desired power level. This may occur prior to commencement of DLN film deposition, during DLN film deposition, after DLN film deposition, or intermittently during DLN film deposition, depending on what kind of film structure and composition are desired. Using DC or RF sputtering, materials of all kinds (metals, ceramics, alloys, etc.) can be used for co-deposition. Other sources of dopant beams may include, but are not limited to thermal evaporation, electron beam evaporation, or ion beams.

The growth conditions for nanocomposite films are the following, with reference to FIG. 4. The pressure in the deposition chamber 1 should not exceed $10^{-3}$ torr, with the pressure in the active zone of the plasma generation 2, in the range from about $1.0 \times 10^{-3}$ to about $5.0 \times 10^{-2}$ torr. The temperature of the substrate should not exceed about 300° C. with the temperature of the cathode filaments being in the range from about 2100° to about 2950° C. The current in the cathode filament is from about 40 to about 130 A, more preferably from about 70 to about 130 A, with the voltage across the filament being from about 5 to about 30 V, more preferably from about 20 to about 30 V. The voltage with respect to the ground is from about 70 to about 200 V, more preferably from about 70 to about 130 V with the plasma current being from about 0.5 to about 20.0 A. The voltage of the substrate holder is from about 0.1 to about 5.0 Kv, with all the carbon-containing and Si-containing species having kinetic energy in the range of from about 100 to about 1200 eV and from about 25 to about 300 eV respectively. The metal beams consist of free atoms or monatomic ions. The kinetic energy of the metal atoms/ions does not exceed about 25 eV. With a precursor flow rate from about 0.5 to about 5.0 cc/hour, the growth rate of the DLN is from about 0.1 to about 2.0 micrometers/hour.

The preferred range of operation for most applications is a pressure of about $1-3 \times 10^{-4}$ Torr, a plasma current of about 1 amp., a filament current of from about 60 to about 75 amp., a substrate voltage of from about 600 to about 1000 V DC, or forward power of about 100 W in RF mode. The preferred frequency for RF mode is from about 90 to about 450 KHz, more preferably from about 90 to about 300 KHz. The preferred magnetron power depends on the type of material, composition and structure desired for the DLN coating.

In a further preferred embodiment, a preferred method of deposition uses a plasma discharge in a triode plasmatron, as shown schematically in FIG. 4, with the plasma energy density above about 5 Kwh/gram-atom of carbon. The charged particles are extracted by a high voltage field in the vacuum chamber and directed onto the substrate. It is preferable that the potential of the substrate holder is from about –0.3 to about +5.0 Kv, and most preferably 1.0+/–0.2 Kv, and varying with a frequency in the range of from about 0 to about 25 Mhz for DC and from about 90 to about 300 KHz for RF. The ratio of the electron emission to the carbon precursor flow in the plasmatron is from about 0.5 to about 1.5 electrons per particle.

A special effort is made to minimize the presence of contaminants in the deposition chamber. These contaminants may include undesired metallic species, water, oxygen, nitrogen or other elements or compounds, the absorption spectra of which, and of the compounds or radicals of which lie in the desired wavelengths where high optical transmission is required. The steps taken in this regard may include operating at lower pressures, flushing with inert gases such as argon, maintaining an extremely clean chamber, ensuring that the diffusion and mechanical pump oils are clean, and other such steps readily apparent to those skilled in the field of minimizing contamination in a vacuum chamber. The level of contaminants present can be monitored using a residual gas analyzer.

Further, the substrate voltage/bias has ann effect on the Si-O to C-H ratio. In order to optimize this ratio, especially for high infrared transmission, the substrate voltage/bias should be in the range of from about 100 to about 700 volts.

Similar specific precautions and steps must be taken to obtain high optical transmission in other spectral ranges as well. In order to modify the refractive index of the coating, dopant species and deposition conditions (including substrate bias voltage) must be selected appropriately.

Figure 2:
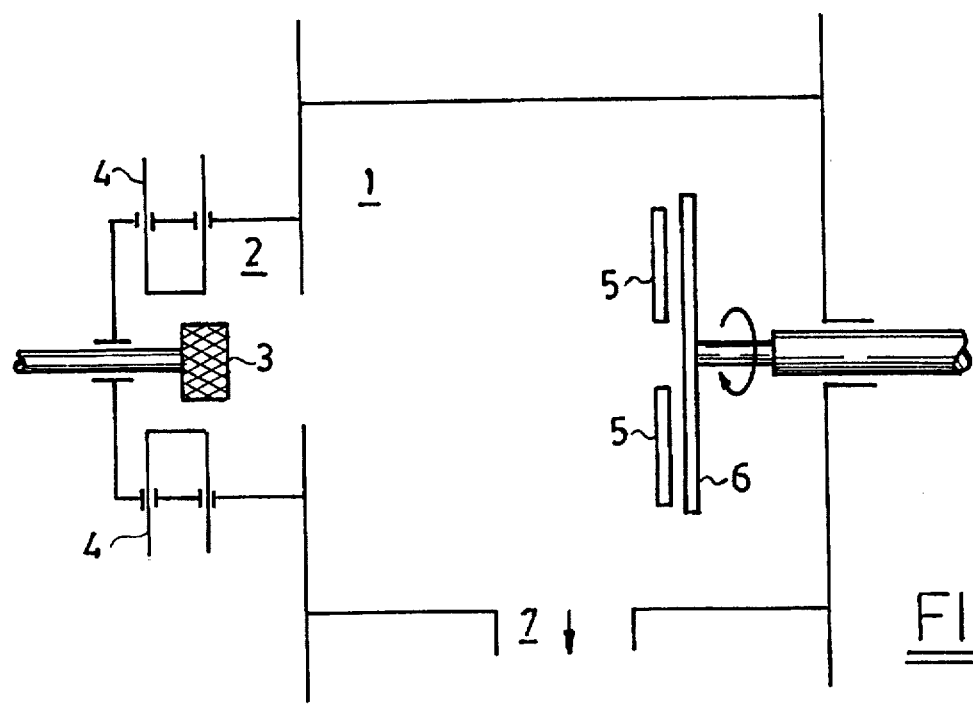
FIG. 2 is a schematic diagram detailing the main method of fabrication of the DLNs.

Organosilicon compounds, such as siloxane, are preferred precursors for C, H, Si and O. One preferred organosilicon compound is polyphenylmethylsiloxane, containing 1 to 10 Si atoms. The high boiling point siloxanes may be introduced directly into the active plasma region through a porous ceramic or metallo-ceramic (3 in FIG. 2 and FIG. 3) which is heated via radiation from thermocathodes 4. The photon and electron emission of the thermocathodes affect the evaporation, fragmentation and ionization of the precursor molecules on the surface of the ceramic, which thereby functions as an ion source for the plasma generator. An alternative method for injection of the siloxane precursors is to use direct injection from a diffusion pump.

The formation of dopant-containing beams may be realized by any one of, or combination of, the following methods: 1) thermal evaporation; 2) ion-sputtering; 3) ion beams. The dopant-containing beams are directed onto the growing film surface through the vacuum chamber to exclude interparticle collisions in the deposition chamber itself. Substrates are placed in an adjacent chamber on a rotating substrate holder, (for example a drum) which ensures double rotary motion, said adjacent chamber being connected to the plasma generation chamber by an opening for the emission of the atomic or ionic beams, as shown schematically in FIG. 3. Alternatively, the plasma generation may be carried out within the chamber containing the substrates (FIG. 4). A DC or a radio frequency potential is generally applied to the substrates during the deposition process. No external substrate heating is required. The substrate holder may be designed specifically to hold parts of different shapes such as cylinders, as would be apparent to one skilled in the field.

It is also understood that for certain desired applications, the dopant containing layers may be alternatively deposited with the non-doped DLN layers. Further, doped-DLN layers with varying amounts of dopant may also be sequentially deposited in series or alternatively with non-doped DLN materials as desired. In a useful variation of the above described methods for deposition of DLN films include the use of sputtered silicon and oxygen gas as precursors for the Si and $O_2$, the use of sputtered carbon and hydrogen or hydrocarbon gas used as carbon and hydrogen precursors, or any combination thereof.

Figure 3:
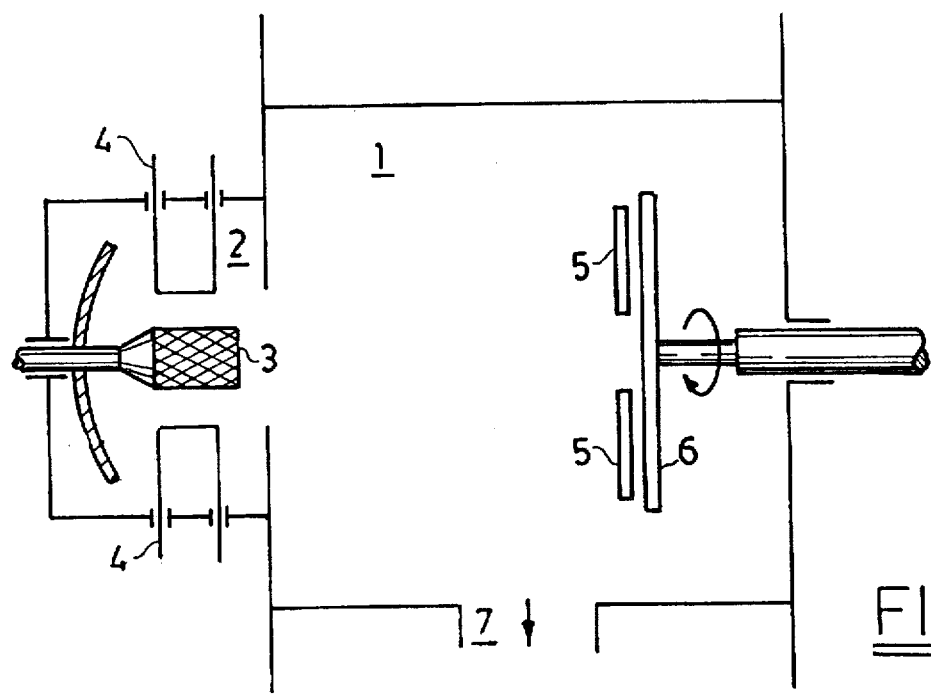
FIG. 3 is a schematic diagram detailing the method of fabrication of DLNs using reflected beam flow.

For deposition on non-conducting substrates, such as plastic, a method whereby a flow of neutral radicals is reflected from a high voltage target and directed to the substrate is shown schematically in FIG. 3. The process employs depositions similarly to those shown in FIG. 2, except that a reflecting electrode 8 is used to generate a neutral beam. This process eliminates surface damage of the substrate resulting from charged and/or fast particles impinging on the substrate during growth.

A preferred method for depositing ultra-thin dielectric DLN films comprises ion bombardment (e.g. $Ar^+$ or $K^+$ with energy in the range of from about 30 to about 150 eV) through a vacuum chamber which has been backfilled by siloxane vapor (about $3 \times 10^{-4}$ torr). This results in a self-stabilized growth of a nanocomposite film, with the maximum thickness controlled by the maximum tunneling distance for the relaxation of the charge of the absorbed radicals.

Extremely uniform and nonporous ultra-thin dielectric films may be deposited according to the present invention.

The thickness of the deposited DLN coating has no theoretical limit. Existing technology and available equipment have allowed atomic-scale composite films and coating thicknesses typically in the range from about 1 μm to about 10 μm. According to the present invention, a film thickness in the range from about 6 to about 8 nm may be deposited, with a deposited film thickness of from about 3 to about 5 nm being preferred.

Therefore, the above-described flexible coatings of the present invention may be deposited on the selected substrate in thicknesses ranging from a few nanometers to a few microns, preferably from about 20 nm to about 12 microns, depending only on the desired application of the coated substrate. The deposition may therefore be tailored or "tuned" to meet the properties required for a particular application. The random interpenetrating of the two- or three-network DLNs guarantee uniform strength of the structures in all directions. The structures are free of micropores even at thicknesses of 80 Angstroms (8 nm). The DLNs are therefore extremely stable and possess unique combinations of chemical, mechanical, electronic, and superconducting properties.

The following examples serve only to further illustrate aspects of the present invention and should not be construed as limiting the invention.

EXAMPLE 1

Deposition of DLN Coating

A two micron thick coating of DLN was deposited on zinc sulfide infrared windows. Windows were cleaned and mounted on the substrate holder in the deposition chamber using metal clips. To clean the substrates, the chamber was closed and pumped down to $5 \times 10^{-5}$ Torr. Argon gas flow was introduced to the chamber and until the pressure within the chamber reached $3.6 \times 10^{-4}$ Torr. Filament current was switched on and increased to 60 amps, while filament bias voltage was −160V and electromagnet current was 250 milliamps. The substrate RF bias was switched on to 100 W forward power at a frequency of 237 kHz. The substrate was rotated and maintained at a speed of 7 rpm. After 5 minutes, of plasma cleaning, the precursor needle valve was opened to a setting of 3 cc/hour. After about 5 minutes, the argon gas flow was stopped. A plasma current of about 1 amp was obtained. Substrate load power was about 80 W. After about 30 minutes of deposition, substrate bias forward and load power were reduced by about 25%. After approximately 3 hours, the precursor valve was closed and the power shut off. The chamber and substrates within were allowed to cool. The chamber was then backfilled with nitrogen and the DLN coated infrared windows removed from the substrate holder.

EXAMPLE 2

Adhesion Properties of DLN Coatings

DLN coatings made and applied to substrates according to the protocol described in Example 1 were tested qualitatively to determine the adhesion of the coatings to various materials. DLN coatings exhibited good to excellent adhesion to the following metal substrates: Li, Al, Ti, Zr, Hf, Nb, Ta, Cr, Mo, W, Re, Fe, Co, Ni, Ag, Cu, etc; the following ceramics: sitall, quartz and aluminum based ceramic substrates, zirconia, metal ceramics, etc.; and the plastic substrates: polyimide, Teflon™, HDPE, polyurethane, glass fiber-resin composites, acrylic, polysilicones, epoxy composites, etc. Table 1 shows subjective comparisons between the adhesion of DLN and DLC coatings to various substrates.

The adhesion problems ordinarily encountered with DLC coatings, such as spalling or chipping, did not occur with the DLN coatings due to their high adhesion properties. The interface of the coating with the substrate material can be specifically tailored by modifying deposition conditions to achieve high degrees of adhesion.

TABLE 1

Adhesion of DLC and DLN Coatings

| Substrate | Adhesion DLC | Adhesion DLN | Min. Interface thickness (nm) DLC | Min. Interface thickness (nm) DLN |
|---|---|---|---|---|
| Steel | ++ | +++ | 20–40 | 2–3 |
| Al | ++ | +++ | — | 3–5 |
| Ti | ++ | +++ | — | 2–3 |
| Cu | — | ++ | — | 5 |
| Au | — | ++ | <25 | 5 |
| Co | — | +++ | — | 5–10 |
| Cr | — | +++ | — | 5–10 |
| Mo | — | +++ | — | 5–10 |
| Ni | — | +++ | — | 5–10 |
| W | + | +++ | 50 | 1 |
| Si | +++ | +++ | >500 | 1–2 |
| Ge | + | ++ | >500 | 2–3 |
| GaAss | + | +++ | 100 | 3–5 |
| Glass | +++ | ++ | — | 10–30 |
| Plastic | + | ++ | — | 10–30 |
| ZnS | — | ++ | — | 5–10 |

EXAMPLE 3

Thermal Shock

The properties of tungsten-doped DLN (W-DLN) thermoresistors did not exhibit a measurable change after $2 \times 10^8$ thermal pulses of nanosecond duration with maximum temperatures above 700° C. No change was determined in the W-DLN after $10^7$ pulses with maximum temperatures above 1200° C. Still further, no change in the W-DLN was determined after single pulse at 1700° C. By contrast, DLC coatings shift to a graphite-like structure at temperature of from about 400°–500° C.

EXAMPLE 4

Mechanical Properties

Samples of aluminum hard-disks were coated with DLN coatings to compare mechanical properties vs. DLC coatings.

A. Coefficient of Friction

The coefficient of friction of the DLNs and DLCs were determined using the ISO test for hard disk coatings. The friction of coefficient of the DLN coatings were two times lower than the DLCs.

B. Hardness and Modulus Tests

Hardness and modulus measurements using a nanoindenter were taken of samples prepared as described in Example 1. The DLNs displayed a hardness of 7–21 GPa and a modulus of 80–200 GPa. The values were found to deteriorate only approximately 10% after exposure to elevated temperatures of from about 400°–500° C.

EXAMPLE 5

Optical Properties

The absorption edge of two-network DLN coincides with the UV-visible boundary (wavelength of about 350 nm).

Optical density is high in the ultraviolet range. Transmission increases monotonically in the visible and near IR range up to a wavelength of about 6 μm. This spectral response depends on the deposition process and can be varied depending upon requirements. High transparency is observed up to approximately 25–40 μm as measured using FTIR spectroscopy. Metal-containing DLNs films (Me-DLNs) possess high absorption which increases with electrical conductivity.

The refractive index (at wavelength 630 nm) is in the range of 1.7 to 2.5 in two-network DLN, depending on the energetic conditions of film growth and precursor species. Refractive index ranges for certain Me-DLN films are listed in the following Table 2. The refractive index and transmission spectrum of DLN coatings can be varied depending on the coating compositions. Transmission of x-rays is also variable and therefore controllable as a function of growth conditions.

TABLE 2

|  | W-DLN | Hf-DLN | Zr-DLN | Al-DLN | Si-DLN | Nb-DLN | Ta-DLN |
|---|---|---|---|---|---|---|---|
| $n_{min}$ | 2.25 | 2.15 | 2.51 | 3.27 | 2.20 | 2.30 | 2.50 |
| $n_{max}$ | 3.90 | 3.10 | 3.10 | 3.69 | 2.74 | 3.80 | 3.10 |

Physical Erosion Testing

COMPARATIVE EXAMPLE A

Figure 5A:
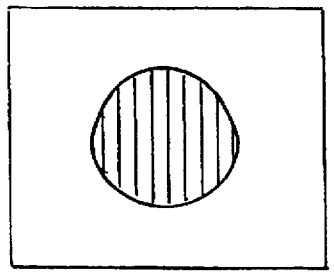
FIGS. 5A–5F show a series of drawings representing the results of abrasion testing on DLN coated and uncoated samples.

A sample of aluminum was subjected to falling sand abrasion test per ASTM D968, Method A. The results of the test are noted in FIG. 5A.

EXAMPLE 6

Figure 5B:
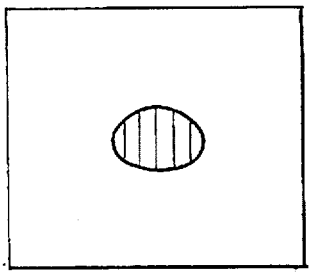

A sample of aluminum coated with an approximately 3 micron thick coating of Hf-DLN was subjected to falling sand abrasion test per ASTM D968, Method A. The results of the test are noted in FIG. 5B.

EXAMPLE 7

Figure 5C:
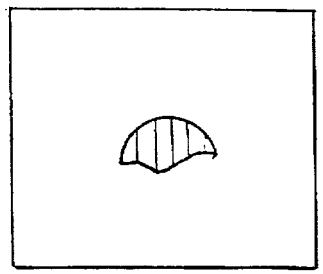

A sample of aluminum coated with an approximately 3 micron thick coating of DLN was subjected to falling sand abrasion test per ASTM D968, Method A. The results of the test are noted in FIG. 5C.

COMPARATIVE EXAMPLE B

Figure 5D:
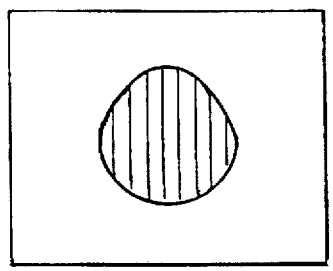

A sample of stainless steel was subjected to falling sand abrasion test per ASTM D968, Method A. The results of the test are noted in FIG. 5D.

EXAMPLE 8

Figure 5E:
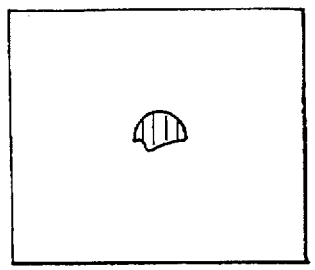

A sample of stainless steel coated with an approximately 3 micron thick coating of Hf-DLN was subjected to falling sand abrasion test per ASTM D968, Method A. The results of the test are noted in FIG. 5E.

EXAMPLE 9

Figure 5F:
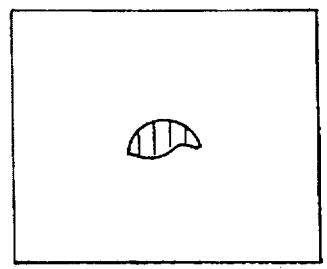

A sample of stainless steel coated with an approximately 3 micron thick coating of DLN was subjected to falling sand abrasion test per ASTM D968, Method A. The results of the test are noted in FIG. 5F.

In all instances of Examples 6–9 and Comparative Examples A–B, the imprint shown in FIGS. 5A–5F is the size and shape of the erosion area on the tested specimens (2"×2"). The volumes listed under FIGS. 5A–5F is the volume of sand used for the test.

Data from the testing of Examples 6–9 and Comparative Examples A–B are further presented in Table 3. For coated specimens, the volume of sand required to abrade through the 3 micron coating was determined. The determination of 'wear-through' is a subjective test made by the unaided eye. For uncoated specimens, since there was no way to measure the depth of the abraded area, the total area of erosion by 2 liters of sand was taken as a qualitative measure of the extent of abrasion. See FIGS. 6A–6F. Following the testing, the erosion area on uncoated aluminum was approximately 3 times that seen on the DLN coated aluminum for the same sand volume. The erosion area on uncoated steel was approximately 6 times that seem on the DLN coated steel for the same sand volume. The erosion test was done at three locations on each sample.

TABLE 3

| | | Comparative Erosion Resistance | | | | | | |
|---|---|---|---|---|---|---|---|---|
| | | Liters of Sand | | | Erosion (μ) | | | Avg. |
| Ex. # | Samp. | Area 1 | Area 2 | Area 3 | Area 1 | Area 2 | Area 3 | liter/μ |
| A | Al | — | 2.00 | — | — | 0.17 | — | 0.17 |
| 6 | Al/Hf-DLN | 1.00 | 1.25 | 1.10 | 0.33 | 0.42 | 0.37 | 0.37 |
| 7 | Al/DLN | 1.50 | 1.50 | 1.40 | 0.5 | 0.5 | 0.47 | 0.49 |
| B | Steel | — | 2.00 | — | — | 0.20 | — | 0.20 |
| 8 | Steel Hf-DLN | 3.00 | 2.65 | 2.65 | 1.00 | 0.88 | 0.88 | 0.92 |
| 9 | Steel/DLN | 1.75 | 2.00 | 1.65 | 0.58 | 0.67 | 0.55 | 0.60 |

Many other modifications and variations of the present invention are possible to the skilled practitioner in the field in light of the teachings herein. It is therefore understood that, within the scope of the claims, the present invention can be practiced other than as herein specifically described.

We claim:

1. An erosion resistant material made from an optically transmissive substrate and an erosion resistant coating, said coating made from a class of diamond-like materials formed from interpenetrating networks, said networks comprising a first diamond-like carbon network stabilized by hydrogen, a second silicon network stabilized by oxygen and, optionally, at least one additional network of dopant elements, or compounds containing elements from groups 1–7b and 8 of the periodic table.

2. The material according to claim 1 wherein the carbon, hydrogen, silicon and oxygen are obtained from the decomposition of an organosiloxane having from about 1 to about 10 silicon atoms.

3. The material according to claim 2 wherein the organosiloxane is polyphenylmethylsiloxane.

4. The material according to claim 1 wherein the carbon content is from about 40 wt. % to about 98 wt. %.

5. The material according to claim 1 wherein the carbon content is from about 50 wt. % to about 98 wt. %.

6. The material according to claim 1 wherein the carbon to silicon weight ratio is from about 2:1 to about 8:1.

7. The material according to claim 1 wherein the silicon to oxygen weight ration is from about 0.5:1 to about 3:1.

8. The material according to claim 1 wherein the dopant elements are selected from the group consisting of B, Li, Na, Si, Ge, Te, O, Mo, W, Ta, Nb, Pd, Ir, Pt, V, Fe, Co, Mg, Mn, Ni, Ti, Zr, Cr, Re, Hf, Cu, Al, N, Ag, and Au.

9. The material according to claim 1 wherein the carbon content of the solid state material is greater than about 40 atomic % of the coating, the hydrogen content is up to about 40 atomic % of the carbon, and the sum of the silicon, oxygen and dopants together is greater than about 2 atomic % of the coating.

* * * * *